(12) United States Patent
Moachon et al.

(10) Patent No.: US 8,118,176 B2
(45) Date of Patent: Feb. 21, 2012

(54) MEMBRANE UNIT ELEMENT, SEMIPERMEABLE MEMBRANE, FILTRATION DEVICE, AND PROCESSES FOR MANUFACTURING THE SAME

(75) Inventors: Nicolas Moachon, Tignieu Jameyzieu (FR); Michel Thomas, Sérézin du Rhône (FR)

(73) Assignee: Gambro AB (SE)

( * ) Notice: Subject to any disclaimer, the term of this patent is extended or adjusted under 35 U.S.C. 154(b) by 0 days.

(21) Appl. No.: 12/557,708

(22) Filed: Sep. 11, 2009

(65) Prior Publication Data
US 2010/0032376 A1 Feb. 11, 2010

Related U.S. Application Data

(62) Division of application No. 10/918,447, filed on Aug. 16, 2004, now abandoned.

(60) Provisional application No. 60/504,194, filed on Sep. 22, 2003.

(30) Foreign Application Priority Data

Aug. 28, 2003 (FR) ...................... 03 10257

(51) Int. Cl.
*B01D 63/02* (2006.01)
*B01D 61/24* (2006.01)
*B01D 69/08* (2006.01)
*B01D 61/28* (2006.01)

(52) U.S. Cl. ........... 210/500.23; 210/321.8; 210/500.37; 210/500.43

(58) Field of Classification Search .................. None
See application file for complete search history.

(56) References Cited

U.S. PATENT DOCUMENTS

| 4,364,759 A | 12/1982 | Brooks et al. |
| 4,871,461 A | 10/1989 | Karakane et al. |

(Continued)

FOREIGN PATENT DOCUMENTS

EP 0 166 237 A2 1/1986

(Continued)

OTHER PUBLICATIONS

English (machine) translation of JP07-100202 (1995).*

(Continued)

*Primary Examiner* — Krishnan S Menon
(74) *Attorney, Agent, or Firm* — Finnegan, Henderson, Farabow, Garrett & Dunner, LLP

(57) ABSTRACT

The object of the invention is a unit element forming a membrane comprising a semi-permeable material able to separate in two compartments a filtration device for extracorporeal treatment of a fluid such as blood or plasma, said material being negatively charged, said element having a first internal face intended to be in direct contact with blood or plasma and a second external face intended to be in contact with filtrate, wherein said second face of said element is treated on the surface by one selected in the group comprising at least a cationic polymer, a mixture of polymers of which at least one polymer is cationic. The unit element can also have said first face treated on the surface by one selected in the group comprising: at least one cationic polymer, a mixture of polymers of which at least one polymer is cationic.

The object of the invention is also a semipermeable membrane consisting of such unit elements; a filtration device for extracorporeal treatment of a fluid such as blood or plasma comprising two compartments separated by such a semipermeable membrane.

The object of the invention is also the processes for manufacturing such devices.

15 Claims, 6 Drawing Sheets

U.S. PATENT DOCUMENTS

| | | |
|---|---|---|
| 5,032,282 A | 7/1991 | Linder et al. |
| 5,089,187 A | 2/1992 | Aptel et al. |
| 5,254,249 A | 10/1993 | Terada et al. |
| 5,393,432 A | 2/1995 | Tsuyumoto et al. |
| 5,407,581 A | 4/1995 | Onodera et al. |
| 5,547,576 A | 8/1996 | Onishi et al. |
| 6,001,288 A | 12/1999 | Saruhashi et al. |
| 6,177,013 B1 | 1/2001 | Thomas et al. |
| 6,248,238 B1 | 6/2001 | Burtin et al. |
| 6,260,715 B1 | 7/2001 | Simard et al. |
| 6,325,218 B1 | 12/2001 | Lee et al. |
| 6,423,232 B1 | 7/2002 | Thomas et al. |
| 7,056,458 B2 | 6/2006 | Crost et al. |
| 7,094,347 B2 | 8/2006 | Wu et al. |
| 2003/0021826 A1 | 1/2003 | Crost et al. |
| 2005/0273031 A1 | 12/2005 | Ueno et al. |

FOREIGN PATENT DOCUMENTS

| | | |
|---|---|---|
| EP | 0 923 955 A2 | 6/1999 |
| EP | 0 925 826 A1 | 6/1999 |
| EP | 0 615 780 B1 | 4/2001 |
| EP | 1 230 940 A1 | 8/2002 |
| FR | 2 817 769 | 6/2002 |
| GB | 1 600 820 | 10/1981 |
| JP | 61-296115 | 12/1986 |
| JP | 5-301031 | 11/1993 |
| JP | 6-349 | 1/1994 |
| JP | 6-7430 | 1/1994 |
| JP | 6-15167 | 1/1994 |
| JP | 7-100202 | 4/1995 |
| JP | 10-328299 | 12/1998 |
| JP | 11-300169 | 11/1999 |
| JP | 11-332979 | 12/1999 |
| JP | 11-332987 | 12/1999 |
| JP | 2003-220134 | 8/2003 |
| WO | WO 95/10349 | 4/1995 |
| WO | WO 01/54802 | 2/2001 |
| WO | WO 03/049775 A2 | 6/2003 |
| WO | WO 2004/018085 A1 | 3/2004 |

OTHER PUBLICATIONS

David A. Pegues, et al., "Anaphylactoid Reactions Associated with Reuse of Hollow-Fiber Hemodialyzers and ACE Inibitors" *Kidney International*, vol. 42 (1992), pp. 1232-1237.

International Preliminary Reprot on Patentability for International Application No. PCT/IB2004/002302.

International Preliminary Report on Patentability for International Application No. PCT/IB2004/002302.

* cited by examiner

State of the art

MEMBRANE UNIT ELEMENT, SEMIPERMEABLE MEMBRANE, FILTRATION DEVICE, AND PROCESSES FOR MANUFACTURING THE SAME

CROSS REFERENCE TO RELATED APPLICATIONS

This is a divisional of application Ser. No. 10/918,447 filed Aug. 16, 2004, now abandoned which claims priority of French patent application No. 03 10257, filed on Aug. 28, 2003 and the benefit of U.S. Provisional Application No. 60/504,194, filed on Sep. 22, 2003, the contents of which are incorporated herein by reference.

TECHNICAL FIELD OF THE INVENTION

The purpose of the present invention is to provide a filtration device, especially useful in the extracorporeal treatment of a fluid such as blood or plasma, a semipermeable membrane mainly consisting of a sheet membrane or hollow fibers conformed from a unit element consisting of a sheet film or a hollow fiber respectively, said unit element and the manufacturing processes of these objects.

PRIOR ART

Filtration devices, for the treatment of blood or plasma by extracorporeal circulation, are used in various medical and paramedical applications such as kidney failure treatment by dialysis, ultrafiltration, haemofiltration or haemodiafiltration, therapeutic and non-therapeutic plasmapheresis and apheresis, blood oxygenation, immunoclearance, etc.

DESCRIPTION OF A FIRST PROBLEM

In patients with renal insufficiency treated for instance by haemodialysis, ultrafiltration, haemofiltration or haemodiafiltration by means of a membrane type exchanger, some unwanted reactions called anaphylactoid reactions are observed.

Such reactions may have very severe consequences that can lead to the patients death. Typically, these reactions show up within a few minutes after the beginning of treatment, by various symptoms, such as the sensation of systemic heat, numbness in fingers, lips or tongue, wheezing, nausea, edema of the larynx, etc.

The anaphylactoid reactions were mainly observed during the use of medical devices such as membrane-type exchangers fitted with membranes made of materials with different chemical compositions, whether during single use or multiple uses.

As examples of exchangers the first use of which was accompanied by an unwanted anaphylactoid reaction, there are the dialyzers with polymethylmethacrylate or polyacrylonitrile membrane.

Anaphylactoid reactions associated with the re-use of dialyzers with cellulose acetate and polysulfone membrane were also widely documented (refer to D. A. P. et al., "anaphylactoid reactions associated with the reuse of hollow fibers hemodialyzers and ACE inhibitors" in Kidney International 42, 1232-1237 (1992)).

These anaphylactoid reactions are caused by an excessive concentration, in the blood or the plasma, of a peptidic substance, bradykinin.

An explanation proposed for the generation of bradykinin is summarized below: the blood of patients treated by extracorporeal circulation, that comes into contact with the negatively charged surface of the membranes of the filtration devices, is the medium where a biological phenomenon called "activation of the contact phase" occurs.

This activation, due to the density of negative charges on the surface of said membranes results in the production of active substances such as kallicrein and factor XIIa from inactive substances such as prekallicrein and factor XII, kallicrein having a catalytic effect on the production of factor XIIa and vice versa. But bradykinin results from the transformation by kallicrein—which takes place during the activation of the contact phase—of a plasma protein, the high molecular weight kinogen.

Complications may develop when the activation of the contact phase occurs when, at the same time, some disturbing factors are present in the blood, e.g.

drug(s) used in the treatment of hypertension by inhibition of the natural mechanism of vasoconstriction, generically referred to as converting enzyme inhibitors or CEIs; these CEIs are also used for other therapeutic applications, in particular for the treatment of certain forms of cardiac incompetence; but the CEIs are also intended to avoid degradation of bradykinin;

diluted blood—this is the dilution of the blood entering a device such as a dialyzer filled with saline solution—and/or a blood pH that is lower than 7.4—the pH reduction results in the amplification of the reaction of activation of the contact phase.

STATEMENT OF A SECOND ISSUE

In the case of filtration devices such as dialyzers, a phenomenon called "pressure crossing" is observed. Indeed, in the major part of the filter the pressures are such that the molecules contained in the blood are filtered to the dialysis fluid. However, in a specific area of the filter, the pressures are such that a backfiltration is observed, i.e. certain modules can transit from the dialysis fluid to the blood.

Accordingly, if the dialyzate quality is generally not very critical due to the low porosity of the membrane in filtration devices such as low-flow or medium-flow dialyzers, the same does not apply to high-flow filtration devices, such as streamline high-permeability haemodiafilters where there is a higher risk of backfiltration.

In case of proven backfiltration,—for example in case of poor bacteriological quality of the dialysis fluid—, endotoxins or fragments of endotoxins migrate from the dialysis fluid to the blood. There is a high risk of inflammatory reaction in the treated patient.

PRIOR SOLUTION KNOWN FOR THE FIRST PROBLEM

Document EP 0.925.826, bearing the Applicant's name, discloses a filtration device for extracorporeal treatment of patient's blood, comprising a negatively charged polyacrylonitrile semipermeable membrane, said membrane being characterized by a surface-limited overall ionic capacity and being treated in the core or in the surface of the membrane with a neutral polymer or a cationic polymer respectively.

Hence, according to this document, such a membrane with such a limited overall ionic capacity may not lead to an activation of the contact phase under normal operating conditions, if the negative charges are neutralized, especially at the membrane surface—since the negative charges might take part in the activation of the contact phase—by combination of said cationic polymer with said membrane.

In the device as disclosed in this document, the treatment only concerns the membrane face that is directly affected by the activation of the contact phase, i.e. the face that will be in contact with the patient's blood.

An inhibition of the contact phase activation is illustrated therein for a hollow fiber dialyzer whose surface area intended to come in contact with the blood is approximately 1.34 m$^2$ and is quantified with the flow potential of +2.7 µV/mm Hg by comparison with a untreated dialyzer (for which said flow potential is −22 µV/mm Hg).

However, recent studies carried out by the Applicant have shown that, in fact, the activation of the contact phase was not fully inhibited.

Indeed, it has been observed that a residual and delayed activation may occur within the first half-hour after the beginning of the treatment. This activation does not occur automatically and it depends on many factors such as, among others, the patient or the filtration device used.

Discomforting clinical symptoms may then occur such as hypertension, diarrhea, etc., even if they are not as severe as those occurring during the immediate contact phase activation.

Therefore, there is a real need for an improved filtration device for extracorporeal treatment of a fluid such as blood or plasma, that is able to overcome the problems encountered in the prior art.

SOLUTIONS OF THE INVENTION

It has been surprisingly discovered on a filtration device fitted with a negatively charged membrane, that a surface treatment with at least one cationic polymer such as a hydrophilic cationic polymer, preferably water-soluble, or a mixture of polymers of which at least one is a cationic polymer, of such a membrane on the external face of the latter, i.e. the face that will be in direct contact with the filtration or dialysis fluid, enables the retention of endotoxins which otherwise would pass in the blood by backfiltration.

Incidentally, its has also been demonstrated that such a membrane treated on its external face and on its internal face shows a capacity of adsorption of improved heparin, which represents a definite advantage over the non-thrombogenicity of the device fitted with such a membrane.

To the best of the Applicant's knowledge, there is no publication until now that describes an artificial kidney-type filtration device that is fitted with a membrane treated this way on its external face and that unexpectedly results in minimizing the risk of endotoxin backfiltration.

This discovery is the basis of this invention.

Moreover, by implementing this discovery on a membrane of a known filtration device whose external face, intended to be in direct contact with blood, is treated on the surface with at least one cationic polymer such as a hydrophilic cationic polymer, preferably water-soluble, or a mixture of polymers of which at least one polymer is cationic, the Applicant has thus developed new products, such as a membrane and a filtration device, the unit element of which is treated on its two faces, internal and external, and hereafter referred to as "two-face".

Surprisingly these products offer in particular the dual advantage of efficiently avoiding the backfiltration of endotoxins as well the delayed occurrence of the contact phase activation.

In addition to these quite advantageous properties, these products also have a capacity of improved heparin absorption.

OBJECTS OF THE INVENTION

Therefore, a first object of this invention is a unit element forming a membrane comprising a semipermeable material able to separate in two compartments a filtration device for extracorporeal treatment of a fluid such as blood or plasma, said material being negatively charged, said element having a first internal face intended to be in direct contact with blood or plasma and a second external face intended to be in contact with filtrate, characterized in that said second face of said element is treated on the surface by at least one cationic polymer or a mixture of polymers of which at least one polymer is cationic. Such an object will be hereafter referred to as "single-face".

Another object of this invention is a unit element as described above the first face of which is also treated on the surface by at least one cationic polymer or a mixture of polymers of which one polymer at least is cationic, hereafter referred to as "two-face".

Still another object of this invention is a semipermeable membrane comprising an assembly of such unit elements.

Still another object of this invention is a filtration device useful for extracorporeal treatment of a fluid such as blood or plasma, comprising two compartments separated by a semipermeable membrane as defined above and mounted in a casing, a first internal compartment being intended for blood or plasma circulation and comprising one or two accesses and a second external compartment being intended for filtrate circulation and comprising one or two accesses, both compartments being also separated by a potting compound, based on an appropriate adhesive compound, intended for making up a sealed partition separating both compartments.

Another object of this invention is a process for manufacturing a unit element, a membrane and a filtration device such as defined above.

The various objects of this invention and some of their variants will be now presented.

According to one preferred embodiment of the invention, said unit element has the following alternative or complementary features:

said membrane material is a homopolymer or an acrylonitrile copolymer;

said material of the membrane is a copolymer of acrylonitrile and at least of one non-ionic and non-ionisable monomer, possibly having units from at least another olefinic unsaturated monomer that is capable of being copolymerized with acrylonitrile;

said material of the membrane is an acrylonitrile copolymer selected from the group consisting of one acrylonitrile copolymer and at least one anionic or anionisable monomer, possibly enclosing units from at least another olefinic unsaturated monomer that is capable of being copolymerized with acrylonitrile;

said at least one anionic or anionisable monomer is an anionic or anionisable olefinic-unsaturated comonomer carrying anionic groups selected from sulfonates, carboxyls, phosphates and sulfates, preferably sulfates;

said comonomer is sodium methallysulfonate;

said at least one cationic polymer is a hydrophilic polymer selected from the group consisting of a polyamine, a diethylaminoethyldextran (DEAE-Dextran) and a polymer and copolymer containing one or more quaternary ammonium groups;

in addition to the already reported preferred features, said material of the membrane has a flow potential greater than zero after sterilization;

the unit element is a hollow fiber that can be obtained by a manufacturing process preferably comprising the steps of:

(i) preparing a polymer solution comprising a material as defined above;

(ii) extruding the resulting product through a die having two concentric nozzles, a fluid being injected in the internal nozzle to form the aperture of the hollow fiber and then thermomechanically treating (e.g.: stretching) the gel fiber leaving the die; and (iii) treating the external face of said hollow fiber by dipping or spraying a solution containing at least one cationic polymer or a mixture of polymers of which at least one polymer is cationic as defined above;

said process includes an additional step of treating the internal face of said hollow fiber with said solution containing at least one cationic polymer or a mixture of polymers of which at least one polymer is cationic;

the unit element is a sheet film and can be obtained by a manufacturing process preferably comprising the steps of:

(i) preparing a polymer solution comprising a material as defined above;

(ii) extruding after filtration and degassing of said polymer solution through a die having the form of a slot on a rotating cylinder; and (iii) treating the external face of said sheet film by atomizing (or dipping or spraying) a solution containing at least one cationic polymer or a mixture of polymers of which at least one polymer is cationic as defined above.

The extrusion process (ii) can comprise a stretching step of about three times and half the obtained film.

said process includes an additional step of treating the internal face of said sheet film obtained by atomizing (or dipping or spraying) with a solution containing at least one cationic polymer or a mixture of polymers of which at least one polymer is cationic.

According to one preferred embodiment, the semipermeable membrane according to this invention has the following alternative or complementary features:

it consists of an assembly of unit elements such as hollow fibers to make up a hollow fiber bundle it consists of an assembly of unit elements such as sheet films to make up a sheet membrane The negatively charged semipermeable membrane can have an overall ionic capacity—or electrical charge—of less than −30 µeq/g of membrane.

The device according to the invention has the following alternative or complementary features:

said filtration device, useful for extracorporeal treatment of a fluid such as blood or plasma, comprises two compartments separated by a semipermeable membrane mounted in a casing, a first internal compartment being intended for blood or plasma circulation and fitted with two accesses and a second external compartment being intended for filtrate circulation and comprising one or two accesses, both compartments being also separated by a potting compound, based on an appropriate adhesive compound, intended for forming as applicable (i) a cylindrical partition separating both compartments of said device containing a semipermeable membrane of the hollow fiber bundle type as defined above or (ii) a tight seal in said device including a semipermeable membrane of the sheet membrane type as defined above.

The process for manufacturing said device of the invention, useful for extracorporeal treatment of a fluid such as blood or plasma, comprising two compartments separated by a semipermeable membrane mounted in a casing, a first internal compartment being intended for blood or plasma circulation and fitted with two accesses and a second external compartment being intended for filtrate circulation and fitted with one or two accesses, both compartments being also separated by a potting compound, intended to form a tight separation, is characterized in that it comprises a step of circulating, in said external compartment, a polymer solution containing at least one cationic polymer or a mixture of polymers of which at least one polymer is cationic Said process for manufacturing a device according to the invention also comprises a step of circulating, simultaneously or not with the circulation in the external compartment, inside said internal compartment a polymer solution containing at least one cationic polymer or a mixture of polymers of which at least one polymer is cationic.

Said process comprises a step of circulating said polymer solution from one end to the other of one of more compartments and then inverting the circulation direction inside the same compartment.

Said process also comprises a step of circulating said polymer solution from one end to the other of one of the compartments in one circulation direction.

Said process also comprises a step of heparinizing the semipermeable membrane consisting, before use, in pre-heparinizing said membrane, or after mounting, in a heparinizing step during the rinsing of said device.

said process comprises a step of gamma-ray sterilization after manufacture of said device.

It is also possible to consider a process for treating a semipermeable membrane not yet inserted in the treatment device as defined above and comprising the same treatment steps as the process for manufacturing the finished device.

DETAILED DESCRIPTION OF THE PRESENT INVENTION

This invention will now be described in a more detailed manner in its preferred embodiments and using examples of embodiments with reference to the appended drawings in which

Figure 1:
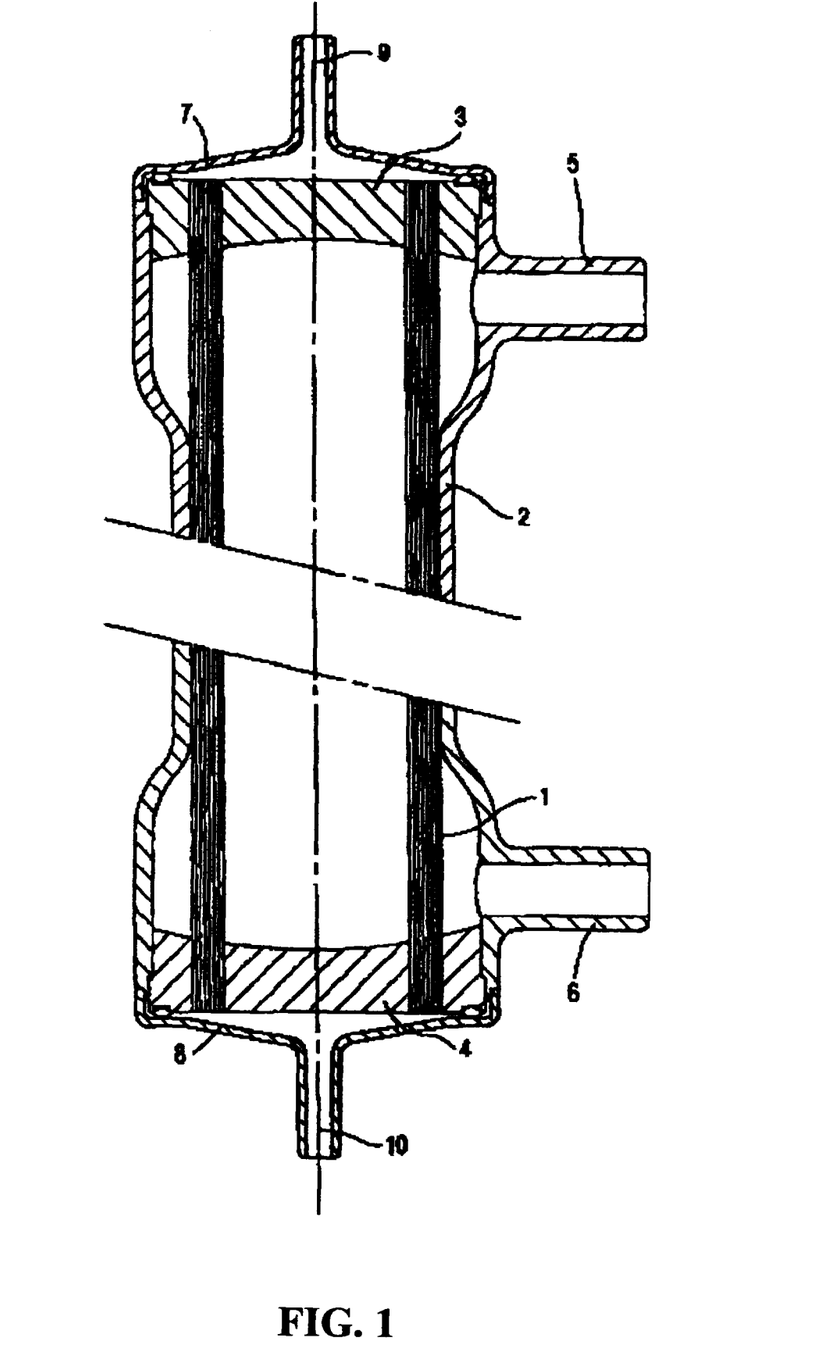
FIG. 1 illustrates a filtration device according to the "two-face" invention for extracorporeal treatment of blood, of the hemodialyzer/haemofilter type.

FIG. 1 illustrates a device according to the invention that is an apparatus for extracorporeal treatment of blood useful to compensate for renal insufficiency.

Such an apparatus conventionally comprises two compartments separated by a semipermeable membrane. A first compartment is intended to be connected through a removal line and a return line to the blood-vessel system of a patient respectively referred to as arterial line and venous line, while the second compartment has an inlet possibly connected to a source of fresh dialysis fluid and an outlet connected to a waste fluid drain line.

The membrane is selected to provide for diffusive and/or convective transfers of metabolic end products, from blood compartment to filtrate compartment.

The membrane can be manufactured from a unit element such as a hollow fiber or a sheet film.

Figure 2:
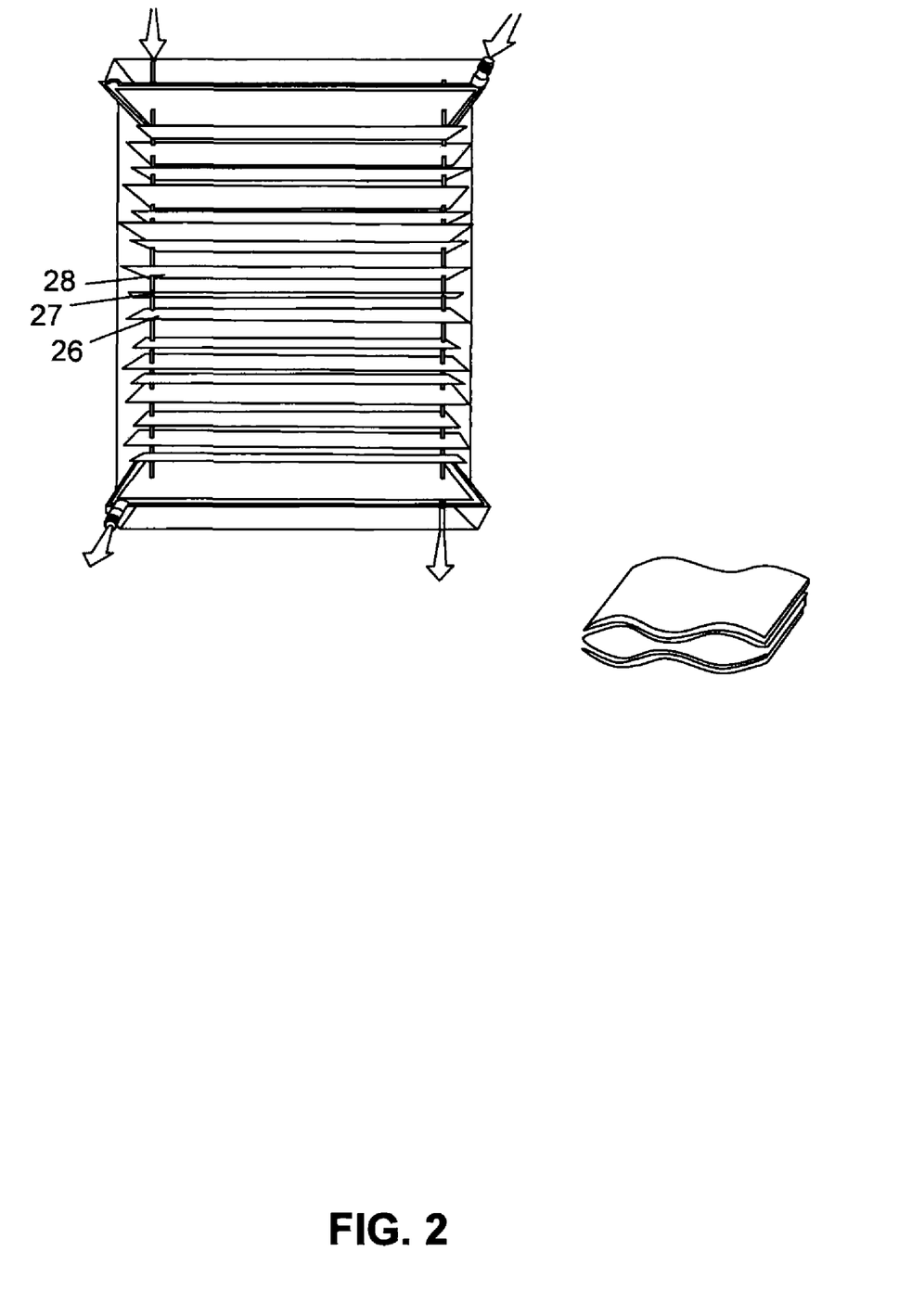
FIG. 2 illustrates a semipermeable membrane according to the invention, of the sheet membrane type made up from unit elements, the sheet films.

For example, a filtration device such as a sheet membrane dialyzer may include a sheet film strip arranged in multiple folds, with a dividing plate inserted in all the folds on the same side (see FIG. 2).

As can be seen in FIG. 1, a filtration device according to this invention comprises a semipermeable membrane such as a hollow fiber bundle (1), which is placed in a tubular enclosure (2) where it is secured at both ends by a disc-shaped partition (3,4). The disc-shaped partitions are not only intended to bind the fibres together, they are also intended to delimit in the tubular enclosure (2) a sealed compartment to which two nozzles (5,6) perpendicular to the centerline of the enclosure (2) give access. To each end of the enclosure (2) is attached and end-fitting (7,8) comprising an axial access nozzle (9,10). Both nozzles (9,10) are symmetric. The blood compartment of the device according to the invention is the inner space between each adhesive disc (3,4) and the end-fitting (8,9) enclosing the corresponding end of the tubular enclosure (2), and from the inside the hollow fibers. The filtrate compartment is the space to which both nozzles (5,6) perpendicular to the centerline of the enclosure (2) give access and comprises the external side of the hollow fibers.

In the scope of this invention:

As a preferred membrane forming material, there is a copolymer of acrylonitrile and sodium methallylsulfonate.

As a preferred cationic polymer useful in the surface treatment according to this invention, there is a high molecular weight polyethyleneimine (PEI).

As other cationic polymers useful in the scope of this invention, there are hydrophilic cationic polymers, highly water-soluble at ambient temperature, such as DEAE-Dextran, and polymers and copolymers containing one or more quaternary ammonium groups.

The "mixture of polymers" preferably consists in the combination of at least one cationic polymer as described above and at least one neutral polymer, highly water-soluble at ambient temperature, such as polyvinylpyrrolidone (PVP), polyethylenegycol (PEG).

When the chemical compound used in the surface treatment is polyethyleneimine (PEI), preferably with an average molecular weight greater than 25,000 Dalton (u), or more preferably greater than 100,000 Dalton (u), it is preferably prepared under the following conditions:

PEI concentration, from 0.04 g/L to 20 g/L
medium: water, glycerinated water, salt buffers, salt solutions
pH: from 7 to 12
treatment flow rates (case of treatment by circulation in filtration device according to this invention: from 50 ml/min. to 500 ml/min.)
in the case of a treatment by spraying, the spraying flow rate will be included between 5 and 100 mg/m$^2$ (PEI concentration between 0.1 and 30 g/l).
time: from 1 to 30 min.
closed or open circuit
under these conditions, the surface concentration of PEI ranges from 1 mg/m$^2$ to 30 mg/m$^2$ In the scope of this invention, the outstanding properties of the objects disclosed therein have been demonstrated using the following test, measurements and/or principles:

In order to show the efficiency of the filtration device of the invention to inhibit the activation of the residual or delayed contact phase, the following test is carried out:

A body fluid, able to stimulate the production of kallicreins (KK) when coming into contact with the membrane negatively charged on the surface, in the sense of the invention is prepared. As a useful liquid for the test, it is possible to use platelet-poor human plasma, diluted 5%. Two liters of this liquid are circulated, in closed circuit at a flow rate of 100 mL/min. in the internal compartment of the device according to the invention.

Plasma kallicreins are measured in the liquid samples taken over time using a conventional chromogenic assay, from substrate S2302 marketed by BIOGENIC.

Thus the increase in kallicrein level (U.K.K/L) over time (min.) is measured in devices according to the invention by comparison with control devices belonging to the prior art.

Measurement of Flow Potentials

The flow potential measurements are useful for comparing membranes with the same mass composition but submitted to different surface treatments.

The electrical potential difference is measured across the terminals of a unit element in the sense of the invention, such as a hollow fiber for instance or across the terminals of a membrane in the sense of the invention, especially, a bundle of parallel hollow fibers, in which circulates an electrolyte, such as a 0.01 M sodium chloride solution.

The flow potential represents the ratio between the measured potential difference and the pressure difference applied to the terminals of the unit element (the fiber) or the fiber bundle (the membrane). It is expressed in µV/mmHg.

Thus the flow potentials in the devices according to the invention are measured by comparison with control devices belonging to the prior art (non treated on the surface or only treated on the face in contact with blood).

Measurement of Heparin Adsorption Capacity

The heparin adsorption capacity is measured during the rinsing of a "two-face" treated device according to the invention and a "single-face on blood side" treated control device belonging to the prior art, with 1 liter of physiological serum containing 5000 UI of non-fractionated heparin with circulation in the internal compartment, "on blood side", open circuit at a flow rate of 150 mL/min.

The capacity of heparin adsorption by the device according to the invention and the control device is assessed by determining heparin concentration in the liquid that circulated in the device (Anti-Xa assay, Stachrom heparin from Diagnostica Stago).

The properties, features and advantages of the objects of the invention will be emphasized in the following non-exhaustive examples only given for reference.

EXAMPLES

Example 1

"Two-Face" Semipermeable Membrane Comprising a Sheet Membrane

A semipermeable membrane of a dialyzer as represented diagrammatically in FIG. 2, is manufactured and treated according to a process including the following steps:
assembly of sheet films (26) previously treated on their internal and external face to achieve a "two-face" dialyzer according to the invention consisting of about 50 sheet films (26) forming parallel blood compartments, the surface area likely to come in contact with blood being approximately 1.53 m²;

water circulation at a flow rate of 150 mL/min for 5 min;

preparation of the PEI solution, with an average molecular weight>750,000 Dalton, obtained by ultrafiltration purification of PEI P from BASF, at a concentration of 0.18 g/L in water and a pH adjusted to 1 with sodium hydroxide; for PEI preparation, also refer to Patent FR 2 804 328 belonging to the same Applicant;

circulation of PEI solution in the internal (27) ("blood side") and external (28) ("dialyzate side") compartments as follows:

flow rate of 300 mL/min., for 5 min.

purging of internal and external compartments with air: 1 min. at an inlet pressure of 400 mmHg; and sterilization by gamma radiation at about 30 kGy.

Instead of being circulated, PEI can also be sprayed on the plates.

The advantage offered by this example is especially the inhibition of the delayed contact phase activation.

Example 2

Conventional filtration device treated according to the state of the art.

Figure 3:
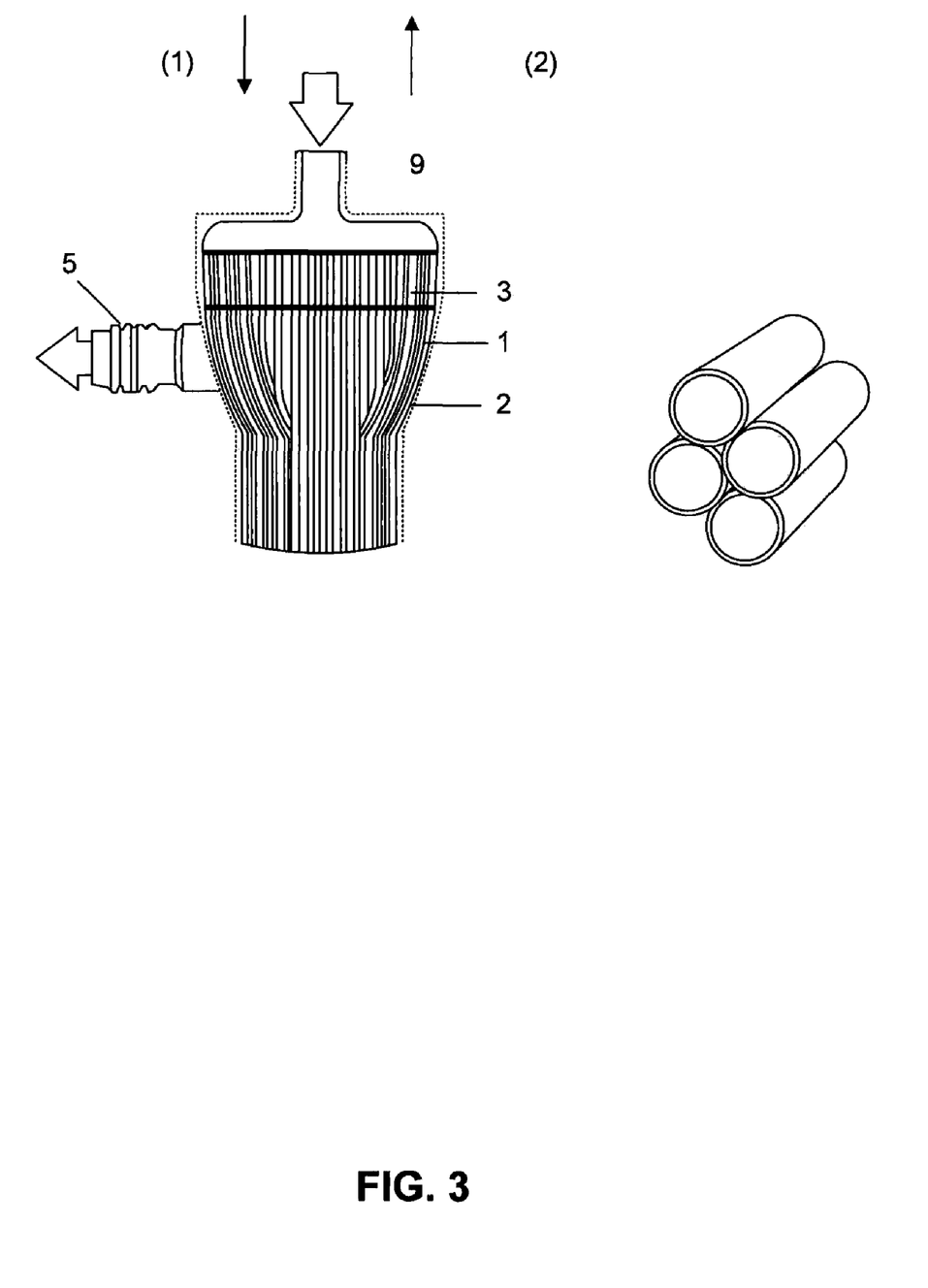
FIG. 3 illustrates a semipermeable membrane according to the invention, assembled from unit elements, the hollow fibers, to form a hollow fiber bundle.

A filtration device such as the hemodialyzer/filter represented diagrammatically in FIG. 1 is manufactured from a membrane of the hollow fiber bundle type as illustrated in FIG. 3.

The internal compartment—in contact with blood—is treated with a series of products manufactured from a semipermeable membrane marketed by GAMBRO under "AN69" reference (registered trademark), i.e. made of copolymer of acrylonitrile and sodium methallyl sulfonate. These products are for instance dialyzers called "NEPHRAL" (registered trademark), also marketed by GAMBRO and corresponding to hollow fiber bundles forming AN69 membrane with a useful surface area ranging from about 1 m² to about 2 m². These "NEPHRAL" dialyzers are fitted with hollow fibers with a length between 220 and 280 mm, an inner diameter of about 220 µm, and a thickness of about 42 µm. The treatment process comprises the following steps:

water circulation at a flow rate of 150 mL/min for 5 min;

identical to the previous example, at a concentration of 0.18 g/L in water and at a pH adjusted to 11 with sodium hydroxide;

circulation of the PEI solution in the internal (1) ("blood side") compartment of the device shown in FIG. 1 as follows:

flow rate of 300 mL/min, for 2.5 min. in direction 1;

flow rate of 300 mL/min, for 2.5 min. in direction 2;

purging of internal compartment (1) with air: 1 min. at an inlet pressure of 400 mmHg; and sterilization by gamma radiation at about 30 kGy.

RESULTS

Measurement of Flow Potentials

Figure 4:
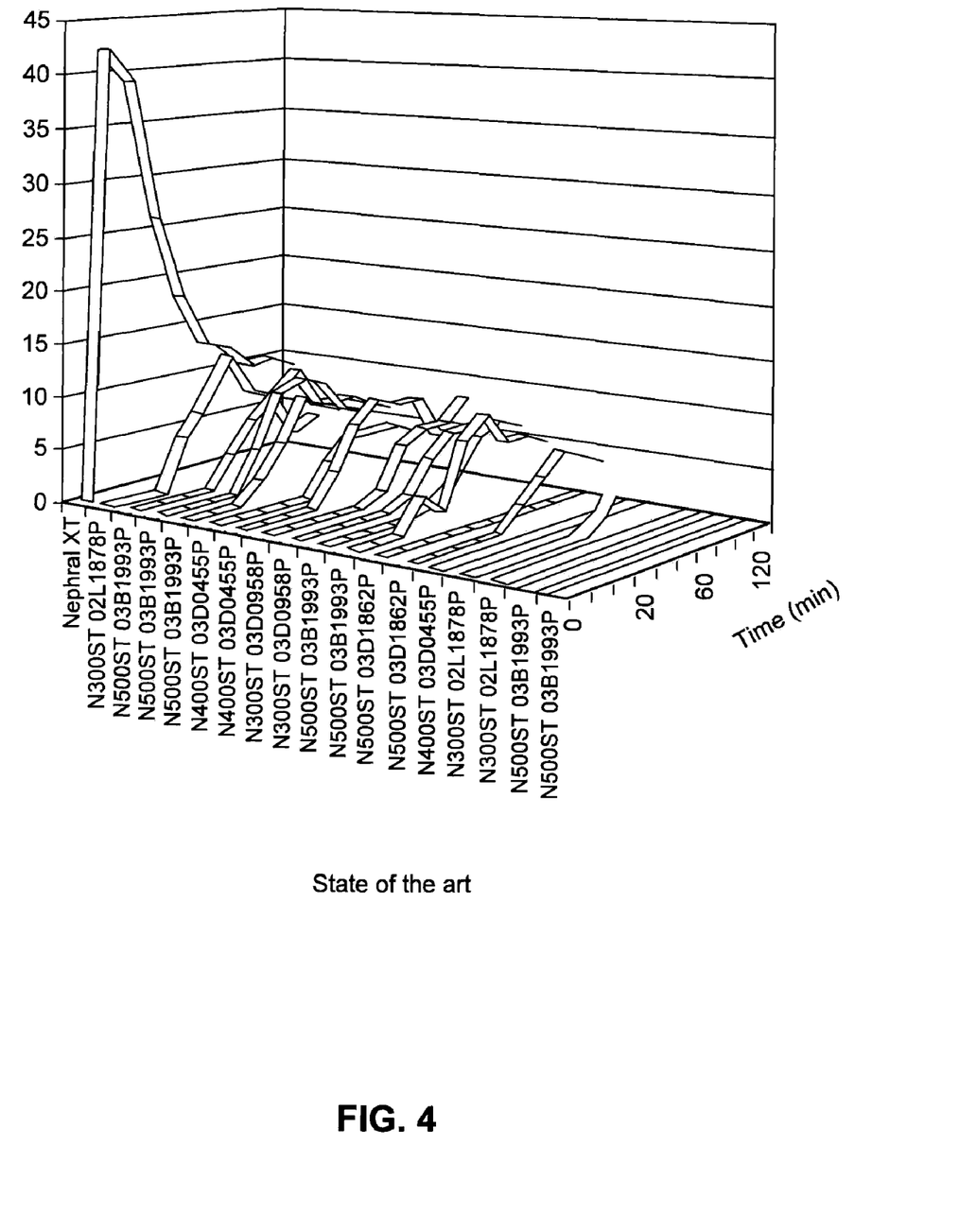
FIG. 4 illustrates the measurement results of the contact phase activation and the finding of a residual and delayed activation of a series of filtration devices whose internal compartment is treated by a process according to the state of the art.

The "blood side" untreated dialyzer referred to as NEPHRAL XT (control) has a flow potential of −20±2 µV/mmHg, while the dialyzers of the NEPHRAL 300, 400 and 500 series, treated according a process of the state of the art "on blood side" as described in Example 3 have a flow potential of −5±2 µV/mmHg after sterilization by gamma radiation Measurement of the Contact Phase Activation As can be seen in FIG. 4, the activation of the contact phase is quantitatively measured with concentration of kallicreins generated as a function of treatment time during the first 2 hours; this applies to several NEPHRAL dialyzers used (N300ST, N400ST and N500ST ranges the series numbers of which are indicated after the range number).

As mentioned above, the activation of the contact phase is delayed because it occurs after the first 20 minutes, but not always since it depends upon several parameters such as the nature of the donor blood for example.

This delayed activation of the contact phase is not quantitatively as severe as the immediate activation in terms of effects on the patient. Indeed, the concentration of the generated kallicreins generated is approximately equal to 10 units.

Thus this example illustrates the activation of the delayed contact phase on the hollow fiber dialyzers according to the state of the art.

Example 3

"Two Face" Filtration Device According to the Invention

The same products as those used in Example 2 undergo the same treatment, except for the sterilization step, then the treatment continues as follows:

treatment with PEI solution as above at a concentration of 0.18 g/L in water and a pH adjusted to 11 with sodium hydroxide in the external compartment ("dialyzate side") of the device as shown in FIG. 3;

flow rate of 300 mL/min. for 5 min.;

purging of the external compartment with air for 1 min. with a pressure of 400 mmHg and sterilization by gamma irradiation at about 30 kGy.

Figure 5:
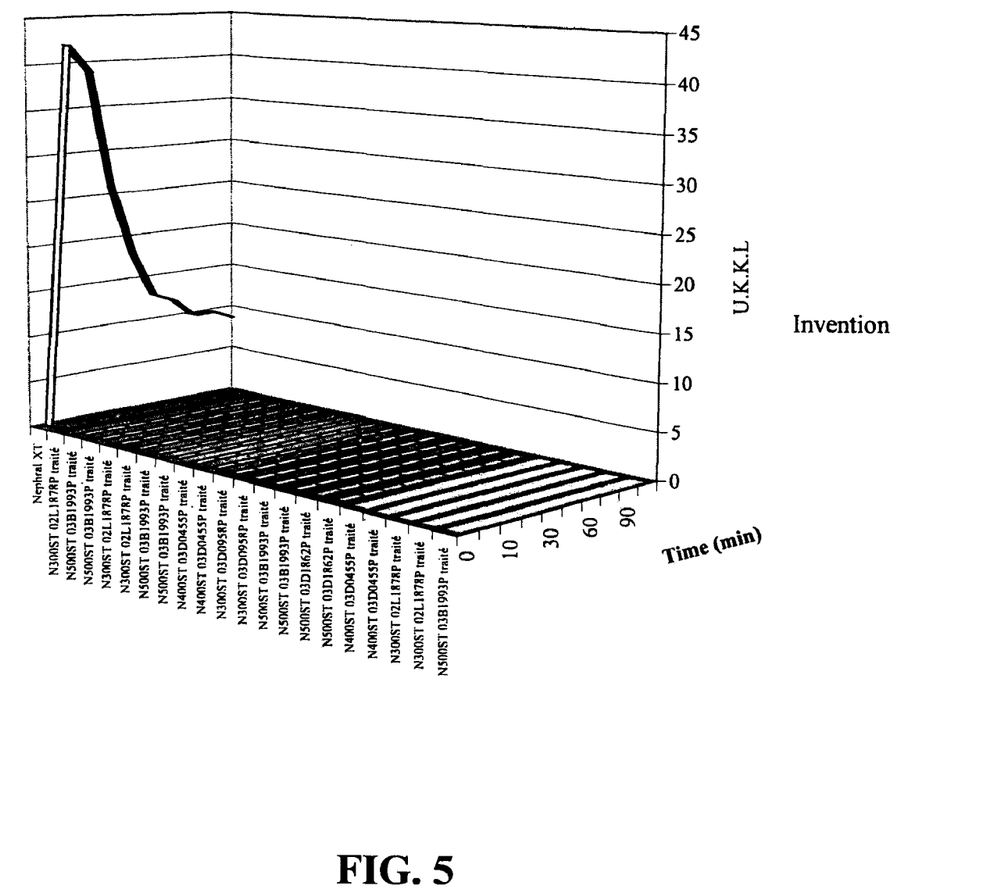
FIG. 5 illustrates the measurement results of the contact phase activation and the finding of such an inhibited residual and delayed activation of a series of "two-face" filtration devices according to this invention whose internal and external compartments are treated according to the invention by comparison with a process according to the state of the art.
Figure 6:
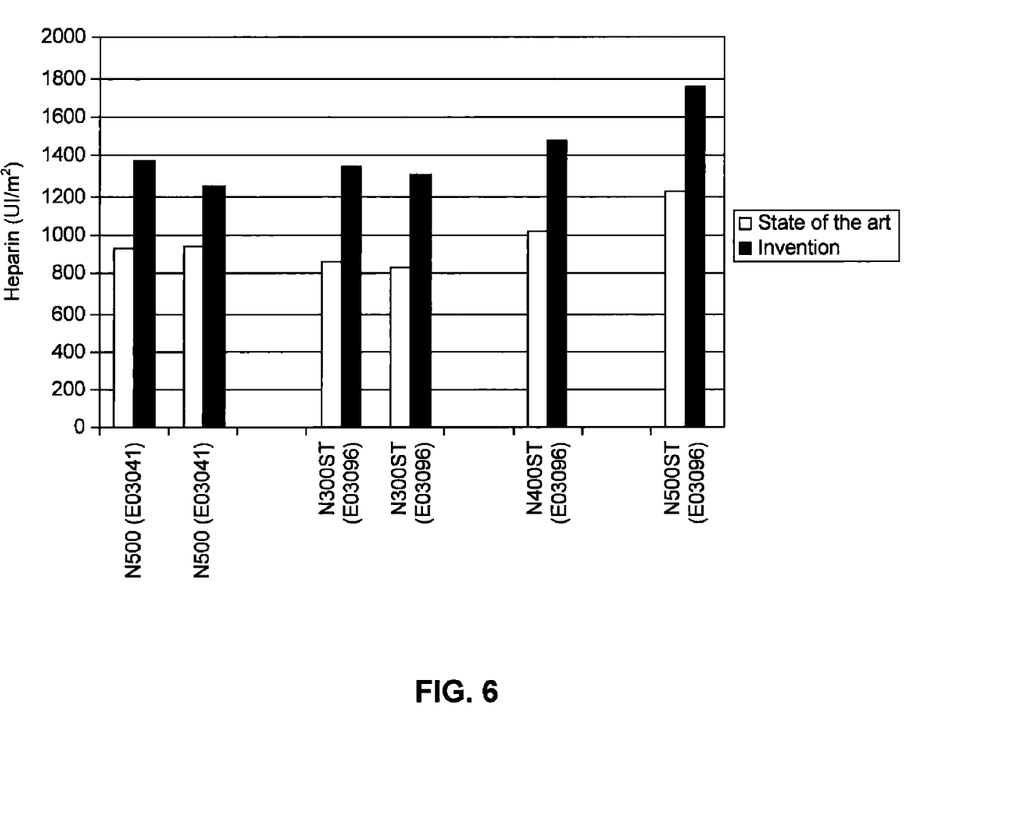
FIG. 6 illustrates heparin adsorption capacity of a series of filtration devices according to the invention with respect to devices treated according to the state of the art.

After sterilization, the resulting "two-face" device according to this invention is characterized by the following outstanding properties:

A flow potential of +5±2 µV/mmHg after sterilization by gamma radiation;

Full inhibition of the residual and delayed activation of the contact phase (as illustrated in FIG. 5); actually, kallicrein generation is no longer observed, even after two-hour treatment;

An improved heparin adsorption capacity (as illustrated in FIG. 6)

The invention claimed is:

1. A method for extracorporeal treatment of a fluid comprising the steps of:

manufacturing a filtration device for extracorporeal treatment of a fluid, said fluid being blood or plasma, the filtration device comprising a first internal compartment and a second external compartment separated by a semipermeable membrane mounted in a casing, said first internal compartment being configured to circulate blood or plasma and said second external compartment being configured to circulate filtrate, wherein the semipermeable membrane comprises a bundle of hollow fibres manufactured according to the steps of:

preparing a polymer solution containing a copolymer of acrylonitrile and at least one of an anionic comonomer and an ionizable comonomer, extruding the prepared polymer solution through a die having two concentric nozzles, a fluid being injected in the internal nozzle to form the lumen of the hollow fiber, thereby forming a gel fiber, and thermomechanically treating the gel fiber leaving the die, and placing the bundle of hollow fibers in a tubular enclosure secured at both ends by a potting compound for binding the fibers together and for tightly sealing in the tubular enclosure the first internal and second external compartments, the first internal compartment being an inner space between each potting compound and a corresponding end-fitting enclosing a corresponding end of the tubular enclosure and the inner space inside the hollow fibers, the second external compartment being the space between an inner side of the tubular enclosure and an external side of the hollow fibers, wherein the method further comprises the steps of:

coating the external side of the hollow fibers by circulating, in said second external compartment, a polymer solution containing at least one cationic polymer or a mixture of polymers of which at least one polymer is cationic and is a hydrophilic polymer selected from the group comprising a polyamine, a diethylaminoethyldextran, and a polymer and copolymer containing one or several quaternary ammonium groups;

circulating the blood or plasma in the first internal compartment;

circulating the filtrate in the second external compartment, the circulating of the blood or plasma in the first internal compartment and the circulating of the filtrate in the second external compartment generating a pressure crossing in the filtration device causing a backfiltration, wherein during the back filtration, molecules contained in the filtrate are filtered to blood or plasma; and preventing endotoxins to pass from the filtrate to blood or plasma during backfiltration.

2. A method according to claim 1, further comprising the steps of circulating said polymer solution from one end of the second external compartment to another end of the second external compartment and following said circulating, inverting the circulation direction of the polymer solution inside the second external compartment.

3. A method according to claim 1, further comprising the step of circulating said polymer solution from one end of the second external compartment to another end of the second external compartment, said circulating occurring in only one direction inside the second external compartment.

4. A method according to claim 1, further comprising the step of coating the inner side of the hollow fibers by circulating, in said first internal compartment, a polymer solution containing at least one cationic polymer or a mixture of polymers of which at least one polymer is cationic and is a hydrophilic polymer selected from the group comprising a polyamine, a diethylaminoethyldextran, and a polymer and copolymer containing one or several quaternary ammonium groups.

5. A method according to claim 4, further comprising the steps of circulating said polymer solution from one end of the first internal compartment to another end of the first internal compartment and following said circulating, inverting the circulation direction inside the first internal compartment.

6. A method according to claim 4, further comprising the step of circulating said polymer solution from one end of the first internal compartment to another end of the first internal compartment, said circulating occurring only in one direction inside the first internal compartment.

7. A method according to claim 1, further comprising the step of heparinizing the semipermeable membrane, said heparinizing including, before use of the filtration device on a machine, pre-heparinizing said membrane, or after mounting the filtration device on a machine, heparinizing said membrane during a rinsing step of said filtration device.

8. A method according to claim 1, further comprising a gamma-ray sterilization step after manufacture of said filtration device.

9. A method according to claim 1, wherein said comonomer comprises units derived from at least another olefinic unsaturated monomer capable of being copolymerized with acrylonitrile.

10. A method according to claim 1, wherein the step of coating the external side of the hollow fibers by circulating a polymer solution consists of only coating the external side of the hollow fibers, the inner side of the hollow fibers not being coated with said polymer solution.

11. A method according to claim 4, wherein the steps of coating the external side and the inner side of the hollow fibers by circulating a polymer solution consists of only coating the external side and inner side of the hollow fibers.

12. A method according to claim 1, further comprising preparing a polymer solution including a polyethylenemine in a fluid chosen in the group consisting of water, glycerinated water, salt buffers and water salt solutions, the polyetheyleneimine being in concentration in the solution from 0.04 g/L to 20 g/L, the pH of the solution being between 7 and 12.

13. A methold according to claim 1, wherein the polymer solution is a combination of the at least one cationic polymer and at least one neutral polymer, highly water-soluble at ambient temperature included in the group consisting of polyvinylpyrrolidone and polyethylenegycol.

14. A method according to claim 1, wherein the polyethyleneimine has an average molecular weight greater than 100,000 Dalton.

15. A method according to claim 1, wherein the step of preparing a polymer solution including a polyethyleneimine comprises circulation in the filtration device with a flow included between 50 ml/min and 500 ml/min for a time period between 1 min and 30 min.

* * * * *

UNITED STATES PATENT AND TRADEMARK OFFICE
CERTIFICATE OF CORRECTION

PATENT NO. : 8,118,176 B2
APPLICATION NO. : 12/557708
DATED : February 21, 2012
INVENTOR(S) : Nicolas Moachon et al.

It is certified that error appears in the above-identified patent and that said Letters Patent is hereby corrected as shown below:

In Claim 12, col. 12, line 33, "polyethylenemine" should read --polyethyleneimine--.

Signed and Sealed this
Twenty-ninth Day of May, 2012

David J. Kappos
*Director of the United States Patent and Trademark Office*